(12) United States Patent
Mach (10) Patent No.: US 10,662,460 B2
(45) Date of Patent: May 26, 2020

(54) METHOD OF ENUMERATING COLIFORM COLONIES

(71) Applicant: 3M INNOVATIVE PROPERTIES COMPANY, St. Paul, MN (US)

(72) Inventor: Patrick A. Mach, Shorewood, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 191 days.

(21) Appl. No.: 15/781,547

(22) PCT Filed: Dec. 6, 2016

(86) PCT No.: PCT/US2016/065044
§ 371 (c)(1),
(2) Date: Jun. 5, 2018

(87) PCT Pub. No.: WO2017/100143
PCT Pub. Date: Jun. 15, 2017

(65) Prior Publication Data
US 2018/0355398 A1  Dec. 13, 2018

Related U.S. Application Data

(60) Provisional application No. 62/263,932, filed on Dec. 7, 2015.

(51) Int. Cl.
*C12Q 1/06* (2006.01)
*C12M 1/12* (2006.01)
*C12M 1/00* (2006.01)
*C12M 1/34* (2006.01)
*C12Q 1/04* (2006.01)

(52) U.S. Cl.
CPC .............. *C12Q 1/06* (2013.01); *C12M 23/04* (2013.01); *C12M 23/22* (2013.01); *C12M 25/06* (2013.01); *C12M 41/34* (2013.01); *C12Q 1/045* (2013.01)

(58) Field of Classification Search
None
See application file for complete search history.

(56) References Cited

U.S. PATENT DOCUMENTS

| 4,565,783 A | 1/1986 | Hansen et al. |
| 5,089,413 A | 2/1992 | Nelson et al. |
| 5,137,812 A | 8/1992 | Matner |
| 5,232,838 A | 8/1993 | Nelson et al. |
| 5,364,766 A | 11/1994 | Mach et al. |
| 6,306,621 B1 * | 10/2001 | Brenner .................. C12Q 1/02 435/38 |
| 9,096,883 B2 * | 8/2015 | Roscoe ..................... C12Q 1/04 |

FOREIGN PATENT DOCUMENTS

| WO | WO 2009/082667 | 7/2009 |
| WO | WO 2010/078284 | 7/2010 |
| WO | WO 2012/161992 | 11/2012 |
| WO | WO 2014/099644 | 6/2014 |

OTHER PUBLICATIONS

Atlas, R., "Coliform Agar ES" in Handbook of Microbiological Media for the Examination of Food, 2d ed., Boca Raton, FL, CRC Press 2006, pp. 100-101.*
Atlas, R.M; Coliform Agar ES Chromocult (Chromocult Coliform Agar ES) (Chromocult Enhanced Selectivity Agar); Handbook of Microbiological Media for the Examination of Food—Second Edition; 2006; pp. 100-101 (XP055350253).
Feng, P. et al.; "Enumeration of *Escherichia coli* and the Coliform Bacteria"; Chapter 4, Bacteriological Analytical Manual; 2002 (16 pgs).
Silva, M.P. et al. "Coliforms at 45 deg C and comparison of most probable number method and petrifilm EC for enumeration of total coliforms and *Escherichia coli* of foods"; Ciencia E Technologia De Alimentos; vol. 26, No. 2; 2006; pp. 352-359 (XP055350264).
Brochure entitled "chromocult—ChromoCult® Coliform Agar ES—For detection of coliforms in waste water and fresh foods"; from Merck KGaA; 2004; 4 pgs (XP055350225) retrieved from internet http//www mibius de/out/oxbasehop/html/0/images/wysiwigpro/ Chromocult_Coliform en_ES_100850_engl; retrieved on Feb. 28, 2017.

* cited by examiner

Primary Examiner — Heidi Reese
(74) Attorney, Agent, or Firm — Eric E. Silverman (57) ABSTRACT

A method of enumerating gas-producing coliform bacteria present in a cultured dairy product is provided. The method can comprise forming a mixture that comprises a predefined quantity of the dairy product and a predefined volume of a diluent; inoculating a thin film culture device with the mixture to form a hydrogel comprising a nutrient medium for growing coliform bacteria, an effective concentration of lactose, and an effective concentration of MOPS; incubating the inoculated thin film culture device under conditions that facilitate growth of a coliform bacterium; and identifying and counting a gas-producing colony present in the inoculated culture device.

18 Claims, 1 Drawing Sheet

METHOD OF ENUMERATING COLIFORM COLONIES

CROSS REFERENCE TO RELATED APPLICATIONS

This application is a national stage filing under 35 U.S.C. 371 of PCT/US2016/065044, filed Dec. 6, 2016, which claims the benefit of U.S. Provisional Patent Application No. 62/263,932, filed Dec. 7, 2015, the disclosure of which is incorporated by reference in its entirety herein.

BACKGROUND

Coliform bacteria are a diverse group of metabolically-related related microorganisms. The group is defined by their ability to ferment lactose, a disaccharide found in milk, to a group of metabolic byproducts that include carbon dioxide gas. Thus, the ability to directly and accurately enumerate coliform bacteria in sample depends upon the ability to detect gas production by isolated colonies of the bacteria.

Thin-film culture devices are conveniently used in place of traditional microorganism enumeration techniques that use, for example, Petri dishes containing agar media. Several examples of such thin-film culture devices are described in U.S. Pat. No. 4,565,783 to Hansen et al. and U.S. Pat. No. 5,364,766 to Mach et al.; which are both incorporated herein by reference in their entirety. In a typical device reported by Hansen et al., a cold-water soluble dry powder containing a gelling agent and microbial growth nutrients is coated on a waterproof substrate. A transparent, read-through cover sheet coated on a surface with an acrylate adhesive containing an indicating dye and powdered gelling agent are attached to the coated substrate.

When the device is used, a predetermined amount of an aqueous sample is typically placed in contact the coated substrate and the cover sheet is placed over the sample and substrate. The aqueous sample hydrates the soluble dry powder which then forms a gelled medium capable of sustaining microbial growth. During the growth period, the indicator dye adhered to the cover sheet reacts in the presence of viable microorganisms to give a detectable response that allows visualization of bacterial colonies which are grown on the culture device.

For the detection of gas-producing bacteria (e.g., CO2-producing coliform bacteria), the construction of the Hansen et al. devices advantageously causes the biogenic gas to be trapped adjacent the gas-producing colony in the gelled medium between the substrate and the coversheet.

SUMMARY

The present disclosure generally relates to a method for culturing and enumerating microorganisms that belong to the coliform group. In addition, the present disclosure relates to a device for enumerating microorganisms in a sample. In particular, the present disclosure relates to an improved method of detecting and enumerating gas-producing coliform bacteria in a thin film culture device.

The present disclosure provides a method of enumerating gas-producing coliform bacteria present in a cultured dairy product. The method can comprise forming a mixture that comprises a predefined quantity of the dairy product and a predefined volume of a diluent; inoculating a thin film culture device with the mixture to form a hydrogel comprising a nutrient medium for growing coliform bacteria, an effective concentration of lactose, and an effective concentration of MOPS; incubating the inoculated thin film culture device under conditions that facilitate growth of a coliform bacterium; and identifying and counting a gas-producing colony present in the inoculated culture device.

In any embodiment of the method, the diluent can comprise MOPS. In any embodiment, a concentration of the MOPS in the diluent can be ≥20 mM and ≤50 mM.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a method of detecting "a" microorganism can be interpreted to mean that the method can detect "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

A "thin film culture device", as used herein, refers to a culture device that comprises a sheet-like substrate attached to a sheet-like coversheet, the substrate and the coversheet each having interior-facing and exterior-facing major surfaces. Adhered to an interior-facing major surface of the substrate and/or the coversheet is a substantially water-free coating that comprises a cold water-soluble gelling agent. Optionally, an interior-facing major surface of the substrate and/or the coversheet has a substantially water-free coating comprising a nutrient medium adhered thereon. Optionally, the nutrient medium and/or the gelling agent may be adhered to an adhesive layer coated on the substrate and/or the coversheet. Optionally, the thin film culture device may further comprise a thin, apertured spacer that is adhered to the interior-facing surface of the substrate or the coversheet. Nonlimiting examples of thin film culture devices are disclosed in U.S. Pat. Nos. 4,565,783; 5,089,413; 5,137,812; and 5,232,838; which are all incorporated herein by reference in their entirety.

A "dairy product", as used herein, refers to a product containing and/or derived from milk. A "cultured dairy product", as used herein, refers to a dairy food that has been fermented with a lactic acid bacterium such as, for example a bacterium belonging to the *Lactobacillus, Lactococcus,* or *Leuconostoc* genera. Cultured dairy products include, but are not limited to, cultured buttermilk, sour cream, cheese, cottage cheese, yogurt, and Acidophilus milk.

"MOPS buffer", "MOPS diluent", "diluent comprising MOPS", and "aqueous solution comprising MOPS", as used herein, refers to a composition that comprises (3-(N-morpholino)propane sulfonic acid). When it is adjusted to a particular pH, the "MOPS buffer", "MOPS diluent", or "aqueous solution comprising MOPS" further comprises a conjugate base of MOPS.

A "coliform bacterium", as used herein, refers to a microorganism belonging to the coliform group of bacteria that are used to indicate the sanitary quality of food, water, and beverages. Bacteria classified in this group are defined by their ability to ferment lactose to acid and gas products. Nonlimiting examples of coliform bacteria include species classified in the *Citrobacter, Enterobacter, Hafnia, Klebsiella, Serratia,* and *Escherichia* genera.

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The figures and the detailed description which follow more particularly exemplify illustrative embodiments. Other features, objects and advantages will become apparent from the description and drawings, and from the claims.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

Coliform bacteria are used to indicate the sanitary quality of foods and beverages (including, for example, milk and water). Although coliform bacteria can be found in aquatic, plant and soil environments, their presence can be an indicator of fecal contamination from warm-blooded animals. The coliform bacteria are commonly detected in samples of food or water by their ability to ferment lactose with the production of acid and gas when incubated at 35-37° C. The coliform bacteria include species from a variety of genera including, for example, *Citrobacter, Enterobacter, Hafnia, Klebsiella, Serratia,* and *Escherichia.*

Methods of enumerating coliform bacteria are known. Exemplary methods of enumerating coliform bacteria can be found in the Bacteriological Analytical Manual (P. Feng et al.; 2002; "Enumeration of *Escherichia coli* and the Coliform Bacteria"; Bacteriological Analytical Manual, Chapter 4; which is incorporated herein by reference in its entirety). The methods include direct count methods of culturing the test samples on agar media or in PETRIFILM dry, rehydratable culture devices. The methods further include Most Probable Number (MPN) estimates obtained by culturing the test samples in broth media. Some regulatory agencies require the detection of gas production from lactose in order to confirm the identity of coliform bacteria.

It is now known that, in at least one selective nutrient medium (e.g., Violet Red Bile-Lactose medium, "VRBL") that is used to culture coliform bacteria in thin film culture devices, the production of gas from the fermentation of lactose by certain coliform bacteria (e.g. *Serratia marcescens*) can be substantially reduced in samples containing cultured dairy products. The inventive method relies on the use of a particular buffer to eliminate the inhibitory effect of the cultured dairy product in the thin film culture device, thereby permitting accurate enumeration of coliform bacteria even when cultured dairy products are present in the sample.

The present disclosure provides an improved method of using a thin film culture device to enumerate colony-forming units of coliform bacteria present in a cultured dairy product. The method involves the use of a MOPS buffer to facilitate fermentation of lactose with the resulting production of $CO_2$ gas. Surprisingly, the MOPS buffer provides improved gas production by certain coliform bacteria in cultured dairy product samples than other buffers of similar strength and pH.

Figure 1:
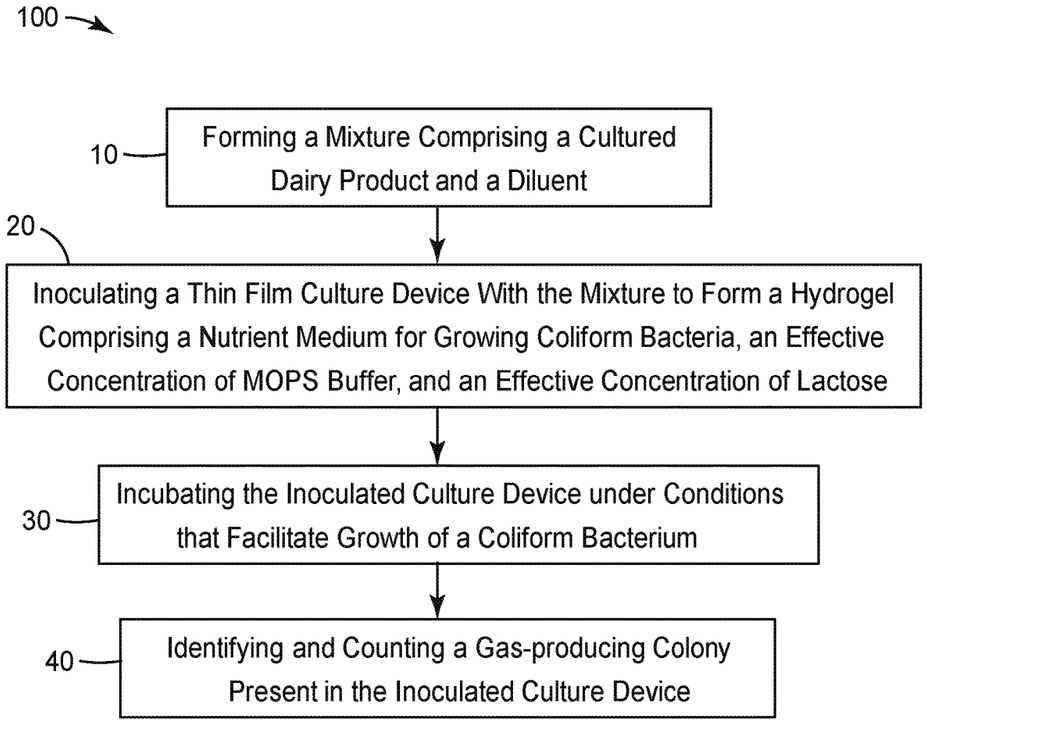
FIG. 1 is a block diagram showing one embodiment of a method of enumerating gas-producing coliform bacteria present in a cultured dairy product according to the present disclosure.

FIG. 1 shows a block diagram of one embodiment of the improved method enumerating in a thin film culture device colony-forming units of coliform bacteria present in a cultured dairy product. The method 100 includes a step 10 of forming a mixture that comprises a cultured dairy product and a diluent. In any embodiment, a predefined quantity of the dairy product can be mixed with a predefined volume of a diluent to form the mixture. Thus, the cultured dairy product is diluted in the diluent and the dilution factor can be recorded and used to calculate the number of coliform bacteria, if any, per gram or milliliter of the original cultured dairy product.

In any embodiment, the dilution factor of the cultured dairy product in the mixture can be about 1:2, about 1:3, about 1:4, about 1:5, about 1:10, about 1:100, about 1:1000, about 1:10000, or about 1:100000, for example.

The cultured dairy product can be any one of a variety of cultured dairy products. Non-limiting examples of cultured dairy products that can be tested using the method include yogurt, cheese, sour cream, buttermilk, curd, leben, calpis, kefir, ayran, qatiq, clabber, and cottage cheese.

Diluents used for suspending and/or diluting food and beverage samples are known in the art and include, for example, distilled water, a buffer, a saline solution, a nutrient medium, and mixtures thereof A preferred diluent according to the present disclosure is a buffered aqueous solution that comprises (3-(N-morpholino)propane sulfonic acid) (hereinafter, "MOPS"). The MOPS may be present in the diluent as the free acid form and/or as a salt (e.g., a sodium salt) of the free acid form of MOPS. A preferred diluent according to the present disclosure is an aqueous buffer solution that comprises a concentration of MOPS effective to facilitate lactose fermentation to gas by colonies of coliform bacteria growing in a thin film culture device. In any embodiment, the diluent can comprise ≥20 mM MOPS. In any embodiment, the diluent can comprise ≤50 mM MOPS. In any embodiment, the diluent can comprise about 20-50 mM MOPS, inclusive. It is contemplated that a aqueous buffered solution comprising MOPS according to the present disclosure may optionally comprise other components such as, for example, a nutrient to facilitate growth of a coliform bacterium and/or a selective agent to inhibit growth of a non-coliform bacterium.

In any embodiment, the diluent comprising MOPS can have a predetermined pH before it is mixed with the cultured dairy product. The concentration of MOPS in the diluent and the pH of the diluent will both influence the pH of the mixture. In any embodiment, the predetermined pH can be >5. In any embodiment, the predetermined pH can be <8. In any embodiment, the predetermined pH can be >5. In any embodiment, the predetermined pH can be ≥5.5 and ≤7.5. In any embodiment, the predetermined pH can be approximately 7.0.

Because the diluent is mixed with the cultured dairy product, the concentration of the MOPS in the mixture may be lower than the concentration of MOPS in the diluent. For example, when a diluent comprising 20 mM MOPS is mixed with a cultured dairy product to produce a mixture in which the cultured dairy product is diluted 1:5, the concentration of MOPS in the mixture is about 16 mM. Accordingly, when a diluent comprising 50 mM MOPS is mixed with a cultured dairy product to produce a mixture in which the dairy product is diluted 1:5, the concentration of MOPS in the mixture is about 40 mM.

In any embodiment, the mixture can be formed in a container (e.g., a dilution bottle, a homogenizer bag). In any embodiment, the mixture can be homogenized (e.g., using a mixing apparatus known in the art) in order to form a more-uniform distribution of the diluent, the sample and any microorganisms, if present therein, so that the microorganisms can be accurately enumerated.

In any embodiment, forming the mixture can comprise forming a mixture having a pH within a predefined range. For example, in any embodiment, forming a mixture having a pH within a predefined range can comprise forming a mixture having a pH >5. In any embodiment, forming a mixture having a pH within a predefined range can comprise forming a mixture having a pH <8. In any embodiment, forming a mixture having a pH between 5.5 and 7.5.

Referring back to FIG. 1, the method 100 further comprises a step 20 of inoculating a thin film culture device with the mixture (i.e., comprising the cultured dairy product and the diluent) to form a hydrogel comprising a nutrient medium for growing coliform bacteria, an effective concentration of lactose, and an effective concentration of MOPS. In any embodiment, forming an inoculated thin film culture device minimally comprises depositing into the thin film culture device the predefined volume of the mixture. The thin film culture device, before inoculation, may comprise the nutrient medium for growing coliform bacteria and/or the lactose. If the thin film culture device, before inoculation, does not comprise the nutrient medium and/or the lactose, they can be provided in the mixture (e.g., as a component of the diluent) or they can be deposited into the thin film culture device (e.g., by pipet) where they can be mixed with the mixture.

Thin film culture devices sold under the trade name PETRIFILM™ E. coli/Coliform Count Plate (Part No. 6404, available from 3M Company, St. Paul, Minn.), PETRIFILM™ Coliform Count Plate (Part No. 6410, available from 3M Company), and PETRIFILM™ High-Sensitivity Coliform Count Plate (Part No. 6405, available from 3M Company), for example, are both suitable for use in the method of the present disclosure. Both aforementioned thin film culture devices include lactose, a nutrient medium for growing coliform bacteria, and a selective agent (bile salts) that inhibits growth of non-coliform bacteria. Prior to inoculation, the lactose, the components of the nutrient medium, and the selective agent are all substantially water-free. When rehydrated with a predefined volume of aqueous sample (e.g., when the thin film culture device is inoculated with the mixture comprising the cultured dairy product and the diluent), a hydrogel is formed in the inoculated device. The hydrogel comprises an effective concentration of lactose and an effective concentration of MOPS according to the method of the present disclosure.

The fabrication of thin film culture devices is described, for example, in U.S. Pat. Nos. 4,565,783; 5,089,413; 5,137,812; and 5,232,838. An effective amount of MOPS or a salt thereof can also be incorporated into such a thin film culture device before inoculation, as described in International Publication No. WO 2012/161992 A1, which is incorporated herein by reference in its entirety. Otherwise, the MOPS can be provided in the diluent that is mixed with the cultured dairy product, as described in the Examples herein.

Thin film culture devices may comprise a substrate (e.g., a self-supporting substrate), a coversheet (e.g., a coversheet through which the interior of the device can be observed), and a dry, rehydratable cold water-soluble gelling agent (e.g., guar gum, xanthan gum, locust bean gum, or mixtures thereof) disposed (e.g., in a coating) between the substrate and the coversheet. Optionally, the thin film culture device, before inoculation, may further include a nutrient, a selective agent, and/or an indicator reagent disposed (e.g., in a coating) between the substrate and the coversheet.

In any embodiment, forming an inoculated thin film culture device comprises depositing (e.g., by pipet) the mixture that comprises the cultured dairy product and the diluent between the substrate and the cover sheet of the thin film culture device. As discussed above, the MOPS buffer may be provided as a component of the thin film culture device or as a component of the diluent used to form the mixture in step 10 of the method 100, as described herein. It is contemplated that, alternatively, the MOPS (e.g., in aqueous solution) could be deposited (e.g., by pipet), separately from the mixture, into the thin film culture device and subsequently mixed with the mixture before closing the inoculated thin film culture device.

It is further contemplated that forming an inoculated thin film culture device further may comprise depositing (e.g., by pipet) into the thin film culture device a nutrient to facilitate growth of a coliform bacterium and/or selective agent to inhibit growth of a non-coliform bacterium. The nutrient and/or selective agent may be present in one or more solution that may be mixed with the mixture after they are deposited into the thin film culture device but before the device is closed.

After inoculation with an aqueous medium (e.g., the mixture of the diluent and the cultured dairy product) that may include a coliform bacterium, the cold water-soluble gelling agent in the thin film culture device contacts the medium and forms a hydrogel. The hydrogel has a quantity of coliform bacteria that, if present in the mixture, reproduce to form colonies in the hydrogel and ferment the lactose in the hydrogel and thereby produce acid and gas products. The gas, which is trapped in the hydrogel proximate the each gas-producing colony, forms observable gas bubbles in the hydrogel proximate the colony that produced the gas. Nutrients and/or selective agents, whether present in the thin film culture device before inoculation or deposited into the thin film culture device during inoculation, diffuse into the hydrogel to form a nutrient medium that enhances growth of coliform bacteria relative to other microorganisms (e.g., lactic acid bacteria) that may be present in the cultured dairy product.

When the hydrogel is formed after inoculation of the thin film culture device, the hydrogel is sandwiched between the coversheet and the substrate.

In any embodiment of the method, inoculating thin film culture device with the mixture to form a hydrogel comprises forming a hydrogel that has an effective concentration of MOPS. In any embodiment, the effective concentration of MOPS in the hydrogel can be ≥16 mM. In any embodiment, the effective concentration of MOPS in the hydrogel can be ≤40 mM. In any embodiment, the effective concentration of MOPS in the hydrogel can be 16-40 mM, inclusive.

Inoculating thin film culture device with the mixture to form a hydrogel comprises forming a hydrogel that has an effective concentration of lactose. The effective concentration of the lactose is sufficient to permit the formation of an observable gas bubble by a lactose-fermenting colony-forming unit of coliform bacteria growing in the thin film culture device. In any embodiment, the effective concentration of lactose in the hydrogel can be ≥0.5% (w/v).

In any embodiment, the effective concentration of lactose in the hydrogel can be ≤1.25% (w/v). In any embodiment, the effective concentration of lactose in the hydrogel can be 0.5% to ≤1.25% (w/v), inclusive.

Referring back to FIG. 1, after inoculating the thin film culture device with the mixture, the method 100 further comprises the step 30 of incubating the inoculated thin film culture device under conditions that facilitate growth of a coliform bacterium. A person having ordinary skill in the art will recognize incubating the inoculated thin film culture device under conditions that facilitate growth of a coliform bacterium can include incubating the inoculated thin film culture device at a temperature that is higher than ambient temperature. Preferably, incubating the inoculated thin film culture device comprises incubating the culture device at a temperature greater than or equal to 30° C. and less than or equal to 44° C. In any embodiment, incubating the inoculated thin film culture device comprises incubating the culture device at a temperature in the range 35-37° C., inclusive.

In any embodiment, incubating the inoculated thin film culture device under conditions that facilitate growth of a coliform bacterium include incubating the culture device for a period of time sufficient to permit formation of an observable colony of the coliform bacteria. The period of time to form an observable colony can be about 4 hours to about 48 hours, inclusive; preferably, about 16 to about 26 hours, inclusive; more preferably, about 18 to about 24 hours. A thin film culture device according to the present disclosure may include an indicator reagent (e.g., a redox dye such as triphenyl tetrazolium chloride, for example; a chromogenic enzyme substrate such as 5-bromo-4-chloro-3-indolyl-β-D-galactopyranoside, for example); or a fluorogenic enzyme substrate (e.g., 4-methylumbelliferyl-β-D-galactopyranoside) that reacts with the coliform bacteria, resulting in the formation of a colored and/or fluorescent product that facilitates observation of the colony. Typically, the accumulation of observable gas bubbles produced by a colony of coliform bacteria growing in a thin film culture device occurs within 16-18 hours of incubation. The gas bubbles may continue to increase in size to some extent during incubation periods that are longer than 18 hours.

After incubating the inoculated thin film culture device for a period of time under conditions that facilitate growth of a coliform bacterium, the method 100 further comprises the step 40 of identifying and counting a gas-producing colony present in the inoculated culture device.

Identifying a colony present in the inoculated culture device can comprise observing the hydrogel formed in the thin film culture device for an indication of a bacterial colony. Colonies can be identified in thin film culture devices, for example, by a color change in the hydrogel associated with a reaction between the bacteria in the colony and an indicator reagent, as described hereinabove.

Identifying a gas-producing colony present in the inoculated culture device can comprise observing a void in the hydrogel caused by a biogenic gas bubble that has displaced a portion of the hydrogel sandwiched between the substrate and the coversheet of the thin film culture device. The biogenic gas bubble typically is proximate the colony that produces it. The void may be observed as a substantially colorless, highly light-transmissive region in the hydrogel. The observation of biogenic gas bubbles in thin film culture devices is described, for example, in International Publication No. WO 2014/099644 A1, which is incorporated herein by reference in its entirety.

The Interpretation Guide provided by the manufacturer for use with PETRIFILM *E. coli*/Coliform Count Plates provides guidance regarding the determination whether a gas bubble observed in a thin film culture device is associated with a particular colony. In part, the guidance relates to the proximity of the gas bubble to a microbial colony. In general, a gas bubble contacting a particular microbial colony is regarded as being associated with (i.e., produced by) the colony. In addition, a gas bubble that is located within a distance equal to about three colony diameters is regarded as being associated with (i.e., produced by) the colony. Thus, a colony having a diameter of 0.5 mm may produce a gas bubble that is located up to about 1.5 mm away from the colony. The location of a gas bubble (e.g., observed as a void in the hydrogel) relative to any proximate microbial colonies is used to determine whether the gas bubble was produced by the microorganisms that form the colony.

Observing a void in the hydrogel can comprise observing a void having a minimum dimension. In any embodiment, observing the void in the hydrogel comprises observing a void that has a dimension of at least 0.5 mm along a straight line that passes through the void. In any embodiment, observing the void in the hydrogel comprises observing a void that has a dimension of at least 1.0 mm along a straight line that passes through the void. In any embodiment, observing the void in the hydrogel comprises observing a void that has a dimension up to 3 mm along a straight line that passes through the void.

In any embodiment, identifying and counting a gas-producing colony present in the inoculated culture device can comprise identifying and counting a colony of coliform bacteria that is associated with a coliform bacteria colony-forming unit present in the cultured dairy product. Thus, a presence of a gas-producing colony in the thin film culture device used in the method of the present disclosure can indicate a presence of a coliform bacterium in the cultured dairy product.

In any embodiment of a method according to the present disclosure, counting a gas-producing colony comprises the counting the gas-producing colony manually. Counting the gas-producing colony manually, as used herein, includes counting the colony with the aid of a device (e.g., a Quebec Colony Counter) that provides illumination and/or magnification of the thin film culture device. Alternatively, in any embodiment of a method of the present disclosure, counting a gas-producing colony comprises counting the gas-producing colony using an automated colony-counting apparatus such as, for example, a PETRIFILM Plate Reader available from 3M Company (St. Paul, Minn.).

A method according to the present disclosure can be used to detect certain species of coliform bacteria wherein lactose fermentation to a gas end product (e.g., $CO_2$) is suppressed in a thin film culture device by the presence of a cultured dairy product in the sample used to inoculate the culture device. A non-limiting example of such coliform bacteria include members of the species Serratia liquefaciens. Other coliform bacteria whose gas production from lactose fermentation may be suppressed by cultured dairy products include members of the species Enterobacter agglomerans (also known as Pantoea agglomerans).

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

The following embodiments are intended to be illustrative of the present disclosure and not limiting.

Exemplary Embodiments

Embodiment A is a method of enumerating gas-producing coliform bacteria present in a cultured dairy product, the method comprising:

forming a mixture that comprises a predefined quantity of the dairy product and a predefined volume of a diluent;

inoculating a thin film culture device with the mixture to form a hydrogel comprising a nutrient medium for growing coliform bacteria, an effective concentration of lactose, and an effective concentration of MOPS;

incubating the inoculated thin film culture device under conditions that facilitate growth of a coliform bacterium; and identifying and counting a gas-producing colony present in the inoculated culture device.

Embodiment B is the method of Embodiment A, wherein the effective concentration of MOPS in the hydrogel is ≥16 mM.

Embodiment C is the method of Embodiment B, wherein the effective concentration of MOPS in the hydrogel is ≤40 mM.

Embodiment D is the method of any one of the preceding Embodiments, wherein the diluent comprises the MOPS.

Embodiment E is the method of Embodiment D, wherein a concentration of the MOPS in the diluent is ≥20 mM.

Embodiment F is the method of Embodiment E, wherein a concentration of the MOPS in the diluent is ≤50 mM.

Embodiment G is the method of Embodiment F, wherein a concentration of the MOPS in the diluent is ≥25 mM and is ≤45 mM.

Embodiment H is the method of any one of the preceding Embodiments, wherein the mixture has a pH>5.

Embodiment I is the method of any one of the preceding Embodiments, wherein the mixture has a pH<8.

Embodiment J is the method of Embodiment I, wherein the mixture has a pH≥5.5 and ≤7.5.

Embodiment K is the cultured dairy product is selected from the group consisting of yogurt, sour cream, buttermilk, curd, leben, calpis, kefir, ayran, qatiq, clabber, and cottage cheese.

Embodiment L is the method of any one of the preceding Embodiments, wherein the effective concentration of lactose in the hydrogel is ≥0.5% (w/v).

Embodiment M is the method of Embodiment L, wherein the effective concentration of lactose in the hydrogel is ≤1.25% (w/v).

Embodiment N is the method of any one of the preceding claims, wherein counting a gas-producing colony comprises counting a colony of the genus Serratia.

Embodiment O is the method of any one of the preceding Embodiments wherein, after inoculating the thin film culture device, the hydrogel comprises a nutrient medium that facilitates growth of coliform bacteria.

Embodiment P is the method of Embodiment O wherein, prior to inoculating the thin film culture device, the culture device comprises at least one nutrient of the nutrient medium.

Embodiment Q is the method of Embodiment P, wherein the at least one nutrient is present in the thin film culture device as a substantially water-free composition.

Embodiment R is the method of any one of the preceding Embodiments wherein, after inoculating the thin film culture device, the hydrogel comprises a selective agent that inhibits growth of non-coliform bacteria.

Embodiment S is the method of Embodiment N wherein, prior to inoculating the thin film culture device, the culture device comprises the selective agent.

Embodiment T is the method of Embodiment S wherein, prior to inoculating the thin film culture device the selective agent is present in the thin film culture device as a substantially water-free composition.

Embodiment U is the method of any one of the preceding Embodiments, wherein incubating the inoculated thin film culture device under conditions that facilitate growth of a coliform bacterium comprises incubating the thin film culture device at a temperature in a range of 35-37° C., inclusive.

Embodiment V is the method of any one of the preceding Embodiments; wherein the thin film culture device comprises a substrate, a coversheet, and a dry, rehydratable cold water-soluble gelling agent disposed between the substrate and the coversheet; wherein inoculating the thin film culture device with the mixture to form the hydrogel comprises forming the hydrogel that contacts the coversheet and the substrate of the device; and wherein identifying a gas-producing colony comprises observing a void in the hydrogel proximate the colony.

Embodiment W is the method of Embodiment V, wherein observing the void in the hydrogel comprises observing a void that has a dimension of at least 0.5 mm along a straight line that passes through the void.

Embodiment X is the method of Embodiment W, wherein the void is disposed in the hydrogel ≤1.5 mm away from a visually-detectable colony of bacteria.

Embodiment Y is the method of any one of the preceding Embodiments, wherein counting a gas-producing colony comprises the counting the gas-producing colony manually.

Embodiment Z is the method of any one of Embodiments A through Y, wherein counting a gas-producing colony comprises counting the gas-producing colony using an automated colony-counting apparatus.

EXAMPLES

Reference Examples 1-9

Enumeration of *Serratia liquefaciens*-Spiked Cultured Dairy Products Diluted into Butterfield's Diluent The thin film culture devices (PETRIFILM™ High-Sensitivity Coliform Count Plates) used in these Examples were obtained from 3M Company. The coliform bacterium (*Serratia liquefaciens*) (ATCC 51814) was obtained from the American Type Culture Collection (Manassas, Va.) was used in the experiments described herein. Butterfield's diluent was obtained from Edge Biologicals (Memphis, Tenn.). Various cultured dairy products (shown in Table 1) were obtained from a retail source.

One part of each dairy product was separately mixed with four parts of diluent (Butterfield's diluent) Thus, the total dilution factor for the cultured dairy product was 1:5. An overnight culture of the *S. liquefaciens* was diluted in Butterfield's diluent and a small volume of the diluted culture was added to each container of diluted cultured dairy product to obtain a mixture containing the diluted dairy product and approximately 50 colony-forming units (CFU) of *S. liquefaciens*. The mixtures were homogenized to more-uniformly disperse the dairy product and the bacteria in the mixture. A portion of the mixture was removed in order to measure the pH.

One milliliter of each mixture was used to inoculate separate PETRIFILM™ High-Sensitivity Coliform Count Plates according to the manufacturer's instructions. After inoculation, the plates were incubated for approximately 24 hours at 35° C. After incubation, the gas-producing colonies coliform colonies were identified manually in the plates according to the manufacturer's instructions and the number of colonies observed on each plate was recorded.

A Reference Control was prepared as described for the Reference Examples except that, instead of preparing the bacteria-spiked mixture with one part cultured dairy product and four parts Butterfield's diluent, the "mixture was prepared with five parts Butterfield's diluent (i.e., there was no cultured dairy product in these samples. The reference control shows how many bacteria could be observed in the samples in the absence of any interference that might occur due to the presence of a cultured dairy product in the sample.

Table 2 lists the pH of each Reference Example and the number of gas-producing colonies observed in each sample that was tested. The data show that each of the samples was spiked with about 35 CFU's of *S. liquefaciens* per milliliter (see Reference Control). The data further show that the addition of a cultured dairy product to each sample lowered the pH of the sample mixture from about 7.8 to about 4.0-5.2. In addition, the data show that the average number of CFU's observed in the samples containing a cultured dairy product was about 25 CFU lower (i.e. about 70% lower) than the Reference Control that had the same diluent but no cultured dairy product therein.

TABLE 1

List of Samples

|  | Yogurt | Fat-Free Yogurt | Buttermilk | Cottage Cheese | Low-fat Cottage Cheese | Fat-free Cottage Cheese | Sour Cream | Low-fat Sour Cream | Fat-free Sour Cream |
|---|---|---|---|---|---|---|---|---|---|
| Reference Example | 1 | 2 | 3 | 4 | 5 | 6 | 7 | 8 | 9 |
| Comparative Examples | 1, 10, 19 | 2, 11, and 20 | 3, 12, and 21 | 4, 13, and 22 | 5, 14, and 23 | 6, 15, and 24 | 7, 16, and 25 | 8, 17, and 26 | 9, 18, and 27 |
| Examples | 1 and 10 | 2 and 11 | 3 and 12 | 4 and 13 | 5 and 14 | 6 and 15 | 7 and 16 | 8 and 17 | 9 and 18 |

TABLE 2

Enumeration of *S. liquefaciens* in samples containing a cultured dairy product diluted in Butterfield's diluent. The average number of CFU per plate in Reference Examples 1-9 was approximately 10. The cultured dairy product in each Reference Example is listed in Table 1. The reported CFU's represent an average of two replicate samples for each condition.

| Sample | pH (sample mixture) | CFU (ave.) |
|---|---|---|
| Reference Control | 7.84 | 35 |
| Reference Example 1 | 4.15 | 0 |
| Reference Example 2 | 4.03 | 0 |
| Reference Example 3 | 4.50 | 45 |
| Reference Example 4 | 5.09 | 9 |
| Reference Example 5 | 5.24 | 14 |
| Reference Example 6 | 5.18 | 9 |
| Reference Example 7 | 4.47 | 7 |
| Reference Example 8 | 4.49 | 2 |
| Reference Example 9 | 4.52 | 0 |

Comparative Examples 1-9

Enumeration of *Serratia liquefaciens*-Spiked Cultured Dairy Products Diluted into Butterfield's Diluent The thin film culture devices, coliform bacterium, Butterfield's diluent, and cultured dairy products used in these Examples were the same as those used in Reference Examples 1-9. The mixtures comprising the cultured dairy product, Butterfield's diluent, and coliform bacteria were prepared as described for Reference Examples 1-9 with the exception that; after mixing the cultured dairy product with the diluent, a small volume (≤1 mL) of 0.1N NaOH was added to the mixture in order to adjust the pH of the mixture to about 7.0.

The thin film culture devices were inoculated and incubated as described for Reference Examples 1-9. After the incubation period, the gas-producing colonies in the thin film culture devices were identified and enumerated as described for Reference Examples 1-9.

A Comparative Control A was prepared as described for the Comparative Examples 1-9 except that, instead of preparing the bacteria-spiked mixture with one part cultured dairy product and four parts Butterfield's diluent, the "mixture was prepared with five parts Butterfield's diluent (i.e., there was no cultured dairy product in these samples. The Comparative Control A shows how many bacteria could be observed in the samples in the absence of any interference that might occur due to the presence of a cultured dairy product in the sample.

Table 3 lists the pH of each Comparative Example and the number of gas-producing colonies observed in each sample that was tested. The data show that each of the samples was spiked with about 35 CFU's of *S. liquefaciens* per milliliter (see Comparative Control A). The data show that the average number of CFU's observed in the samples containing a cultured dairy product was about 11 CFU lower (i.e. about 35% lower) than the Comparative Control A that had the same diluent but no cultured dairy product therein.

TABLE 3

Enumeration of *S. liquefaciens* in samples containing a cultured dairy product diluted in Butterfield's diluent, followed by pH adjustment. The average number of CFU per plate in Comparative Examples 1-9 was approximately 19. The cultured dairy product in each of the Comparative Examples is listed in Table 1. The reported CFU's represent an average of two replicate samples for each condition.

| Sample | pH (sample mixture) | CFU (ave.) |
|---|---|---|
| Comparative Control A | 7.06 | 31 |
| Comparative Example 1 | 7.04 | 25 |
| Comparative Example 2 | 6.90 | 25 |
| Comparative Example 3 | 6.98 | 47 |
| Comparative Example 4 | 7.20 | 12 |
| Comparative Example 5 | 7.13 | 4 |
| Comparative Example 6 | 6.93 | 1 |
| Comparative Example 7 | 7.05 | 22 |
| Comparative Example 8 | 6.83 | 23 |
| Comparative Example 9 | 7.10 | 3 |

Comparative Examples 10-18

Enumeration of *Serratia liquefaciens*-Spiked Cultured Dairy Products Diluted into a Diluent Comprising 20 mM Phosphate The thin film culture devices, coliform bacterium, and cultured dairy products used in these Examples were the same as those used in Reference Examples 1-9. The diluent (20 mM potassium phosphate, pH 7.05) was prepared using reagent grade dipotassium hydrogen phosphate. The mixtures comprising the cultured dairy product, the phosphate buffer diluent, and coliform bacteria were prepared as described for Reference Examples 1-9.

The thin film culture devices were inoculated and incubated as described for Reference Examples 1-9. After the incubation period, the gas-producing colonies in the thin film culture devices were identified and enumerated as described for Reference Examples 1-9.

A Comparative Control B was prepared as described for the Comparative Examples 10-18 except that, instead of preparing the bacteria-spiked mixture with one part cultured dairy product and four parts 20 mM phosphate buffer diluent, the "mixture was prepared with five parts 20 mM phosphate buffer diluent (i.e., there was no cultured dairy product in these samples). The Comparative Control B shows how many bacteria could be observed in the samples in the absence of any interference that might occur due to the presence of a cultured dairy product in the sample.

Table 4 lists the pH of each Comparative Example and the number of gas-producing colonies observed in each sample that was tested. The data show that each of the samples was spiked with about 29 CFU's of *S. liquefaciens* per milliliter (see Comparative Control B). The data show that the average number of CFU's observed in the samples containing a cultured dairy product was about 15 CFU lower (i.e. about 52% lower) than the Comparative Control B that had the same diluent but no cultured dairy product therein.

TABLE 4

Enumeration of *S. liquefaciens* in samples containing a cultured dairy product diluted in 20 mM phosphate buffer diluent. The average number of CFU per plate in Comparative Examples 10-18 was approximately 14. The cultured dairy product in each of the Comparative Examples is listed in Table 1. The reported CFU's represent an average of two replicate samples for each condition.

| Sample | pH (sample mixture) | CFU (ave.) |
|---|---|---|
| Comparative Control B | 7.02 | 29 |
| Comparative Example 10 | 4.86 | 0 |
| Comparative Example 11 | 4.79 | 0 |
| Comparative Example 12 | 6.00 | 57 |
| Comparative Example 13 | 6.34 | 4 |
| Comparative Example 14 | 6.58 | 18 |
| Comparative Example 15 | 6.52 | 4 |
| Comparative Example 16 | 6.15 | 15 |
| Comparative Example 17 | 5.84 | 16 |
| Comparative Example 18 | 5.66 | 0 |

Comparative Examples 19-27

Enumeration of *Serratia liquefaciens*-Spiked Cultured Dairy Products Diluted into a Diluent Comprising 35 mM Phosphate The thin film culture devices, coliform bacterium, and cultured dairy products used in these Examples were the same as those used in Reference Examples 1-9. The diluent (35 mM potassium phosphate, pH 7.01) was prepared using reagent grade dipotassium hydrogen phosphate. The mixtures comprising the cultured dairy product, the phosphate buffer diluent, and coliform bacteria were prepared as described for Reference Examples 1-9.

The thin film culture devices were inoculated and incubated as described for Reference Examples 1-9. After the incubation period, the gas-producing colonies in the thin film culture devices were identified and enumerated as described for Reference Examples 1-9.

A Comparative Control C was prepared as described for the Comparative Examples 19-27 except that, instead of preparing the bacteria-spiked mixture with one part cultured dairy product and four parts 35 mM phosphate buffer diluent, the "mixture was prepared with five parts 35 mM phosphate buffer diluent (i.e., there was no cultured dairy product in these samples). The Comparative Control C shows how many bacteria could be observed in the samples in the absence of any interference that might occur due to the presence of a cultured dairy product in the sample.

Table 5 lists the pH of each Comparative Example and the number of gas-producing colonies observed in each sample that was tested. The data show that each of the samples was spiked with about 33 CFU's of *S. liquefaciens* per milliliter (see Comparative Control C). The data show that the average number of CFU's observed in the samples containing a cultured dairy product was about 21 CFU lower (i.e. about 64% lower) than the Comparative Control C that had the same diluent but no cultured dairy product therein.

TABLE 5

Enumeration of S. liquefaciens in samples containing a cultured dairy product diluted in 35 mM phosphate buffer diluent. The average number of CFU per plate in Comparative Examples 19-27 was approximately 12. The cultured dairy product in each of the Comparative Examples is listed in Table 1. The reported CFU's represent an average of two replicate samples for each condition.

| Sample | pH (sample mixture) | CFU (ave.) |
| --- | --- | --- |
| Comparative Control C | 7.01 | 33 |
| Comparative Example 19 | 5.78 | 0 |
| Comparative Example 20 | 5.41 | 0 |
| Comparative Example 21 | 6.36 | 32 |
| Comparative Example 22 | 6.49 | 0 |
| Comparative Example 23 | 6.50 | 21 |
| Comparative Example 24 | 6.59 | 15 |
| Comparative Example 25 | 6.49 | 19 |
| Comparative Example 26 | 6.20 | 0 |
| Comparative Example 27 | 6.12 | 0 |

Examples 1-9

Enumeration of *Serratia liquefaciens*-Spiked Cultured Dairy Products Diluted into a Diluent Comprising 20 mM MOPS The thin film culture devices, coliform bacterium, and cultured dairy products used in these Examples were the same as those used in Reference Examples 1-9. The diluent (20 mM MOPS, pH 7.04) was prepared using reagent grade MOPS free acid and MOPS sodium salt. The mixtures comprising the cultured dairy product, the diluent comprising MOPS, and coliform bacteria were prepared as described for Reference Examples 1-9.

The thin film culture devices were inoculated and incubated as described for Reference Examples 1-9. After the incubation period, the gas-producing colonies in the thin film culture devices were identified and enumerated as described for Reference Examples 1-9.

An Example Control 1 was prepared as described for the Examples 1-9 except that, instead of preparing the bacteria-spiked mixture with one part cultured dairy product and four parts 20 mM MOPS diluent, the "mixture was prepared with five parts 20 mM MOPS diluent (i.e., there was no cultured dairy product in these samples). The Example Control 1 shows how many bacteria could be observed in the samples in the absence of any interference that might occur due to the presence of a cultured dairy product in the sample.

Table 6 lists the pH of each Example and the number of gas-producing colonies observed in each sample that was tested. The data show that each of the samples was spiked with about 29 CFU's of *S. liquefaciens* per milliliter (see Example Control 1). The data show that the average number of CFU's observed in the samples containing a cultured dairy product was only about 7 CFU lower (i.e. about 24% lower) than the Example Control 1 that had the same diluent but no cultured dairy product therein.

TABLE 6

Enumeration of *S. liquefaciens* in samples containing a cultured dairy product diluted in 20 mM MOPS buffer diluent. The average number of CFU per plate in Examples 1-9 was approximately 22. The cultured dairy product in each of the Examples is listed in Table 1. The reported CFU's represent an average of two replicate samples for each condition.

| Sample | pH (sample mixture) | CFU (ave.) |
| --- | --- | --- |
| Example Control 1 | 7.05 | 29 |
| Example 1 | 4.56 | 0 |
| Example 2 | 4.56 | 0 |
| Example 3 | 6.18 | 51 |
| Example 4 | 6.43 | 15 |
| Example 5 | 6.55 | 40 |
| Example 6 | 6.66 | 26 |
| Example 7 | 5.87 | 15 |
| Example 8 | 5.70 | 35 |
| Example 9 | 5.76 | 13 |

Examples 10-18

Enumeration of *Serratia liquefaciens*-Spiked Cultured Dairy Products Diluted into a Diluent Comprising 35 mM MOPS The thin film culture devices, coliform bacterium, and cultured dairy products used in these Examples were the same as those used in Reference Examples 1-9. The diluent (35 mM MOPS, pH 7.03) was prepared using reagent grade MOPS free acid and MOPS sodium salt. The mixtures comprising the cultured dairy product, the diluent comprising MOPS, and coliform bacteria were prepared as described for Reference Examples 1-9.

The thin film culture devices were inoculated and incubated as described for Reference Examples 1-9. After the incubation period, the gas-producing colonies in the thin film culture devices were identified and enumerated as described for Reference Examples 1-9.

An Example Control 2 was prepared as described for the Examples 10-18 except that, instead of preparing the bacteria-spiked mixture with one part cultured dairy product and four parts 35 mM MOPS diluent, the "mixture was prepared with five parts 35 mM MOPS diluent (i.e., there was no cultured dairy product in these samples). The Example Control 2 shows how many bacteria could be observed in the samples in the absence of any interference that might occur due to the presence of a cultured dairy product in the sample.

Table 7 lists the pH of each Example and the number of gas-producing colonies observed in each sample that was tested. The data show that each of the samples was spiked with about 46 CFU's of *S. liquefaciens* per milliliter (see Example Control 2). The data show that the average number of CFU's observed in the samples containing a cultured dairy product was only about 4 CFU lower (i.e. about 9% lower) than the Example Control 2 that had the same diluent but no cultured dairy product therein.

TABLE 7

Enumeration of S. liquefaciens in samples containing a cultured dairy product diluted in 35 mM MOPS buffer diluent. The average number of CFU per plate in Examples 10-18 was approximately 42. The cultured dairy product in each of the Examples is listed in Table 1. The reported CFU's represent an average of two replicate samples for each condition.

| Sample | pH (sample mixture) | CFU (ave.) |
| --- | --- | --- |
| Example Control 2 | 7.08 | 46 |
| Example 10 | 5.79 | 38 |
| Example 11 | 5.79 | 38 |
| Example 12 | 6.44 | 44 |
| Example 13 | 6.62 | 45 |
| Example 14 | 6.74 | 38 |
| Example 15 | 6.79 | 42 |
| Example 16 | 6.56 | 47 |
| Example 17 | 6.42 | 42 |
| Example 18 | 6.48 | 42 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A method of enumerating gas-producing coliform bacteria present in a cultured dairy product, the method comprising:
   forming a mixture that comprises a quantity of the dairy product and a volume of a diluent, wherein the diluent comprises MOPS at a concentration of ≥20 mM and ≤50 mM;
   inoculating a thin film culture device with the mixture to form a hydrogel comprising a nutrient medium for growing coliform bacteria, and sufficient lactose to permit formation of an observable gas bubble by a lactose-fermenting colony of the coliform bacteria, and;
   incubating the inoculated thin film culture device under conditions that facilitate growth of a coliform bacterium; and
   identifying and counting a gas-producing colony present in the inoculated culture device.

2. The method of claim 1, wherein the gas-producing coliform bacteria comprises *Serratia liquefaciens*.

3. The method of claim 1, wherein the effective concentration of MOPS in the hydrogel is ≤40 mM.

4. The method of claim 1, wherein the concentration of the MOPS in the diluent is ≥25 mM and is ≤45 mM.

5. The method of claim 1, wherein the mixture has a pH between 5.0 and 8.0.

6. The method of claim 1, wherein the cultured dairy product is selected from the group consisting of yogurt, sour cream, buttermilk, curd, leben, calpis, kefir, ayran, qatiq, clabber, and cottage cheese.

7. The method of claim 1, wherein the concentration of lactose in the hydrogel is ≥0.5% (w/v).

8. The method of claim 7, wherein the concentration of lactose in the hydrogel is ≤1.25% (w/v).

9. The method of claim 1, wherein counting a gas-producing colony comprises counting a colony of the genus *Serratia*.

10. The method of claim 1 wherein, after inoculating the thin film culture device, the hydrogel comprises a nutrient medium that facilitates growth of coliform bacteria.

11. The method of claim 1 wherein, after inoculating the thin film culture device, the hydrogel comprises a selective agent that inhibits growth of non-coliform bacteria.

12. The method of claim 11 wherein, prior to inoculating the thin film culture device, prior to inoculating the thin film culture device, the culture device comprises the selective agent.

13. The method of claim 12, wherein the selective agent is present in the thin film culture device as a substantially water-free composition.

14. The method of claim 1, wherein incubating the inoculated thin film culture device under conditions that facilitate growth of a coliform bacterium comprises incubating the thin film culture device at a temperature in a range of 35-37° C., inclusive.

15. The method of claim 1, wherein the thin film culture device comprises a substrate, a coversheet, and a dry, rehydratable cold water-soluble gelling agent disposed between the substrate and the coversheet; wherein inoculating the thin film culture device with the mixture to form the hydrogel comprises forming the hydrogel that contacts the coversheet and the substrate of the device; and wherein identifying a gas-producing colony comprises observing a void in the hydrogel proximate the colony.

16. The method of claim 15, wherein observing the void in the hydrogel comprises observing a void that has a dimension of at least 0.5 mm along a straight line that passes through the void.

17. The method of claim 16, wherein the void is disposed in the hydrogel <1.5 mm away from a visually-detectable colony of bacteria.

18. The method of claim 1, wherein counting a gas-producing colony comprises counting the gas-producing colony using an automated colony-counting apparatus.

* * * * *